(12) United States Patent
Paskalov et al.

(10) Patent No.: US 7,989,673 B2
(45) Date of Patent: Aug. 2, 2011

(54) HIGH ENERGY DISINFECTION OF WASTE

(76) Inventors: George Paskalov, Torrance, CA (US); Mark Gorodkin, Los Angeles, CA (US); Viktor Sokolov, Sherman Oaks, CA (US)

( * ) Notice: Subject to any disclaimer, the term of this patent is extended or adjusted under 35 U.S.C. 154(b) by 2405 days.

(21) Appl. No.: 10/698,867

(22) Filed: Oct. 30, 2003

(65) Prior Publication Data

US 2004/0141876 A1 Jul. 22, 2004

Related U.S. Application Data

(63) Continuation-in-part of application No. 10/432,208, filed as application No. PCT/US01/49310 on Dec. 20, 2001, now Pat. No. 7,291,314.

(60) Provisional application No. 60/258,208, filed on Dec. 27, 2000.

(51) Int. Cl.
  *A62D 3/19* (2007.01)
  *A61L 2/00* (2006.01)
  *C07C 1/00* (2006.01)
  *H05F 3/00* (2006.01)

(52) U.S. Cl. .................... 588/311; 422/23; 204/157.15; 204/164

(58) Field of Classification Search .................. 588/311; 422/23; 204/157.15, 164
See application file for complete search history.

(56) References Cited

U.S. PATENT DOCUMENTS

| | | | |
|---|---|---|---|
| 4,954,320 A | 9/1990 | Birmingham et al. | ... 422/186.04 |
| 5,387,324 A | 2/1995 | Ibbott et al. | .................. 204/150 |
| 5,624,544 A | 4/1997 | Deguchi et al. | ............... 205/742 |
| 5,656,171 A | 8/1997 | Strachwitz | .................... 210/695 |
| 5,711,950 A | 1/1998 | Lorenzen | ..................... 424/401 |
| 5,824,353 A | 10/1998 | Tsunoda et al. | ............... 426/66 |
| 5,866,010 A | 2/1999 | Bogatin et al. | ............... 210/695 |
| 5,876,663 A * | 3/1999 | Laroussi | ......................... 422/23 |
| 5,965,009 A | 10/1999 | Shimamune et al. | ......... 205/742 |
| 5,997,590 A | 12/1999 | Johnson et al. | ................ 44/301 |
| 6,033,678 A | 3/2000 | Lorenzo | ....................... 424/401 |
| 6,165,339 A | 12/2000 | Ibbott | .......................... 204/554 |
| 6,284,054 B1 | 9/2001 | Galvin | ............................ 134/10 |
| 6,379,539 B1 * | 4/2002 | Ubelhor | ....................... 210/104 |

FOREIGN PATENT DOCUMENTS

JP  11-253522  9/1999

* cited by examiner

*Primary Examiner* — Edna Wong

(57) ABSTRACT

An apparatus subjects fluid waste to waves from an RF plasma. This allows continuous production of "activated water" characterized by cluster sizes below about 4 molecules per cluster, water having pH below 4 or above 10, or water having ORP of less than −350 mV or more than +800 mV. The basic frequency of the plasma is preferably between 0.44 MHz and 40.68 MHz, and the plasma is preferably modulated at a frequency between 10 kHz and 34 kHz. Flow rates typically range from 20 1/hr to about 2000 1 hr.

9 Claims, 1 Drawing Sheet

HIGH ENERGY DISINFECTION OF WASTE

This application is a Continuation-In-Part of application Ser. No. 10/432208 filed May 20, 2003 now U.S. Pat No. 7,291,314, which claims priority to PCT patent application number PCT/US01/49310 filed on Dec. 20, 2001, which claims benefit of Application No. 60/258208 filed Dec. 27, 2000.

FIELD OF THE INVENTION

The field of the invention is waste disinfection.

BACKGROUND

Fluid organic waste typically contains a high degree of microorganisms. Much of this waste is disposed of into waterways through sewers and into the ground through septic tanks, leach lines and so on. In any case, the microorganisms ultimately infect our potable water causing it to become unhealthy for consumption.

In some instances steps are taken to disinfect the fluid waste before disposal. Many disinfection systems use chemicals to kill some of the microorganisms, but these systems are relatively ineffective because the fluid waste is so highly contaminated to begin with. There are, however, disinfection systems that attempt to separate components of the waste and to dispose of the more contaminated products in a different way than the less contaminated components. U.S. Pat. No. 6,284,054, for example, teaches a system in which solid animal waste is separated from waste water using electrocoagulation. Thereafter, the solid waste is disposed of using incineration or other methods while the waste water is purified and then recycled.

Methods of purification and disinfection often utilize can also utilize filters, reverse osmosis, ion exchange and even ultraviolet waves. Some of these methods, however, have proven to be relatively ineffective in terms of removing a high percentage of microorganisms while others are problematic due to clogging and high expense.

Ion exchange and ultraviolet systems generally work well, however, it is desirable to be able to produce small cluster water defined herein to mean a size of only 5-6 water molecules per cluster, and these methods are not effective at producing such results. Small cluster water is reported to have numerous useful characteristics. Among other things, small cluster water is said to provide: improved taste of foods; accelerated absorption of drugs and food through the digestive tract; and prevention of cancer due to reduced production of mutagens in the intestines and reduced activity of enteric microorganisms and digestive tract tissue cells. See U.S. Pat. No. 5,824,353 to Tsunoda et al. (October 1998). Tsunoda et al. and all other publications identified herein are incorporated by reference in their entirety.

In producing small cluster water, electrical, magnetic, chemical, and acoustical methods have all been utilized. Electrical and magnetic methods typically involve running water past closely spaced electrodes. Examples are set forth in U.S. Pat. No. 5,387,324 (February 1995) and U.S. Pat. No. 6,165,339 (December 2000), both to Ibbott. Usually field strength is adjusted by moving the electrodes or magnets with respect to one another. See, e.g., U.S. Pat. No. 5,866,010 to Bogatin et al. (February 1999). In other instances field strength is adjusted by altering the path of the water. See e.g. U.S. Pat. No. 5,656,171 to Strachwitz (August 1997), which describes curved piping through magnetic field. U.S. Pat. No. 6,033,678 (March 2000) and U.S. Pat. No. 5,711,950 (January 1998) both to Lorenzen, describe production of reduced cluster water by passing steam across a magnetic field.

Chemical methods typically involve adding electrolytes and polar compounds. The U.S. Pat. No. 5,824,353 patent to Tsunoda, et al. teaches production of reduced cluster size water using a potassium ion concentration of 100 ppm or more, and containing potassium ions, magnesium ions and calcium ions in a weight ratio of potassium ions:magnesium ions:calcium ions of 1: 0.3-4.5:0.5-8.5. Other chemical methods include use of surfactants, and clathrating structures that cause inclusion of one kind of molecules in cavities or lattice of another. See U.S. Pat. No. 5,997,590 to Johnson et al. (issued December 1999).

Acoustical methods typically involve subjection of water to supersonic sound waves. See U.S. Pat. No. 5,997,590 to Johnson et al. (issued December 1999).

A Japanese company currently sells a water purifying system that is said to produce water having cluster size of 5-6 molecules. The system, marketed under the name Microwater™, passes tap water past electrodes. Water passing closer to a positive electrode tends to become acidic. The company's literature reports that the acidic water (termed oxidized or hyperoxidized water) is said to be useful as an oxidizing agent to sterilize cutting boards and treat minor wounds. Other suggested uses are treating athlete's foot, minor burns, insect bites, scratches, bedsores and post-operative wounds. The company's literature also reports that the acidic water has been used agriculturally to kill fungi and other plant diseases. Water passing closer to a negative electrode tends to become alkaline. The alkaline water (termed reduced water) is said to be beneficial when taken internally. Such water is said to inhibit excessive fermentation in the digestive tract by indirectly reducing metabolites such as hydrogen sulfide, ammonia, histamines, indoles, phenols, and scatols.

U.S. Pat. No. 5,624,544 to Deguchi et al. (April 1997) describes such a system. Deguchi et al. Claim that oxidizing streams down to pH 4.5 and reducing streams up to pH 9.5 can be achieved on a continuous basis, but that waters having pH 2.5 to 3.2 or pH 11.5 to 12.5 cannot be produced continuously for a long period. It is thought that these limitations are due to the known methods and apparatus being incapable of efficiently reducing the cluster size below about 4 molecules per cluster.

Thus, there is still a need to provide methods and apparatus for dispensing potable liquids that can continuously produce substantial quantities of water having little or no bacteria, having cluster sizes below about 4 molecules per cluster, and all without substantially changing the pH. Water having these characteristics is thought to be more healthy than other water.

SUMMARY OF THE INVENTION

The present invention provides methods and apparatus for treating fluid waste with an RF plasma generator. The fluid waste, usually including waste water, is carried past the waves with a conduit. In a preferred class of embodiments, the system is inline downstream of a toilet. In another aspect, the RF plasma can be housed within a sewer system or in a sanitary fixture.

Methods of reducing biological contamination in waste include the steps of providing an RF plasma wave generator, and carrying the waste past waves produced by the generator under conditions that inactivate or kills a substantial percentage of the microbe content in the waste. Various objects, features, aspects, and advantages of the present invention will

DETAILED DESCRIPTION

Figure 1:
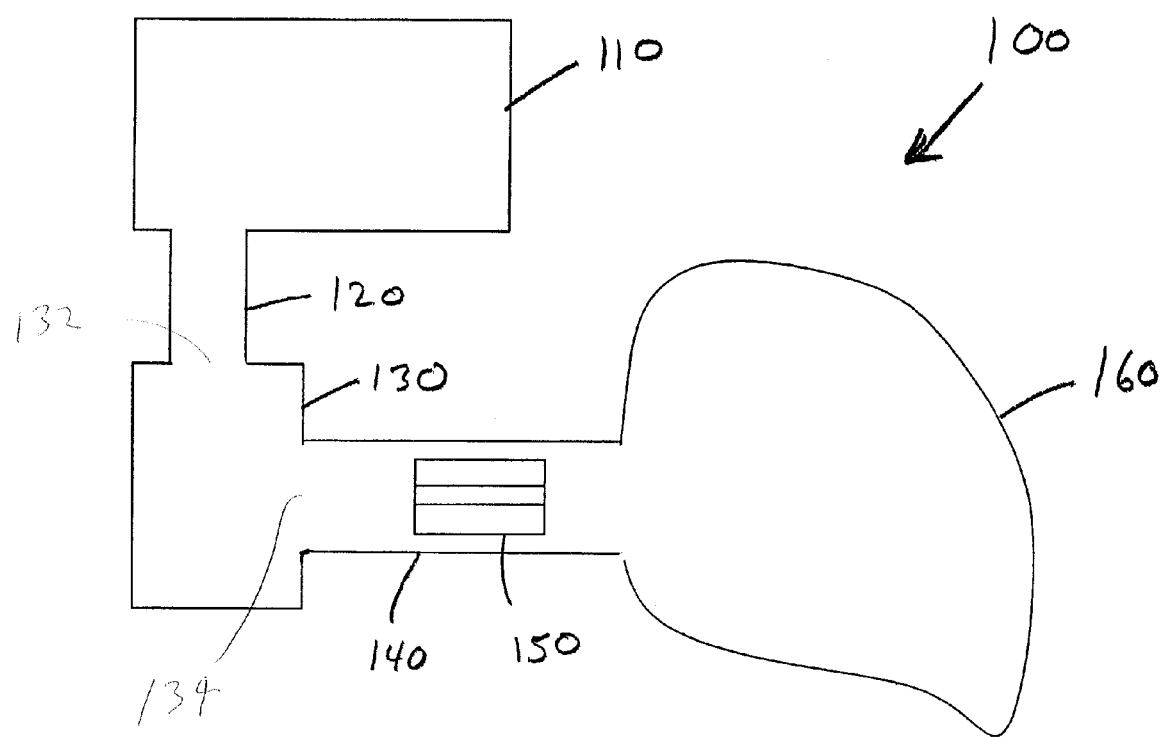
FIG. 1 is a cross sectional view of a system for treating a fluid waste.

Referring first to FIG. 1, a system for treating a fluid waste generally comprises a source of waste 110, a waste line 120, a holding tank 130, a conduit 140, an RF plasma generator 150, and an body including treated waste 160.

Fluid waste encompasses any substantially organic fluid that is in need of disposal such as the waste from the human body and unwanted food. While fluid waste is likely to comprise at least some solid and semi-solid compositions, the solid and semi-solid compositions are insubstantial enough such that the waste is still able to flow through a conduit. In some cases, the assistance of a pump or similar device may be used to push or pull the waste through the conduit.

Fluid waste generally flows into a waste line 120 (e.g. a pipe from a toilet or a sink disposal) and then into a sewer or a holding tank such as a septic tank for a home or a holding tank of a vehicle. Ships, recreation vehicles, and airplanes are good examples of vehicles that have holding tanks. Holding tank 130 has an input at input value 132 and an output at output valve 134. Fluid waste flows into the holding tank 130 through one-way input valve 132. Fluid waste presumably contaminated with a high content microorganisms can be held in a tank for hours, days, or more.

Upon release of the fluid waste from the tank through one-way output valve 134, the waste flows into conduit 140 where it is carried past the waves of the RF plasma generator 150. It should be noted that waste can be carried past the waves in at least two substantially separate streams (i.e. a basic stream and an acidic stream) and then recombined after being subjected to the waves. The basic frequency of the plasma is preferably between 0.44 MHz and 40.68 MHz, and the plasma is preferably modulated at a frequency between 10 kHz and 34 kHz. Flow rates typically range from 20 l/hr to about 2000 l/hr, although multiple configurations and sizes of device are also contemplated, so that lower and higher flow rates are possible.

Conduit 140 is preferred to be a pipe or series of pipes that accepts fluid waste from a holding tank or directly from a source of fluid waste. The conduit, which is substantially water tight, carries the fluid waste past the waves allowing it to be subjected to the waves for an amount of time that is sufficient to inactivate or kill a substantial amount of the microorganisms in the waste. A substantial amount is considered to be 50% although preferred embodiments kill or inactivate over 90%.

Plasmas are conductive assemblies of charged particles, neutrals and fields that exhibit collective effects. Plasma generator 150 is preferably a "cold" type plasma device, which term is used herein to mean a gas of ionized atoms cooler than 10,000° K. With the plasma generator 150 in operation, a stream of fluid waste enters the conduit 140 at output 134, flows through the conduit 140, and exits through outlet 142. It should be noted that multiple inputs and multiple online sources are also contemplated. Moreover, the conduit may accept input from multiple sources.

The RF plasma generator is generally located downstream of a sanitary fixture but may even be located in the fixture itself. In other contemplated embodiments, an RF plasma is in the waste line, in the holding tank, or anywhere else upstream of the treated waste discharge. Specific aspects of an RF plasma wave generator are taught in pending U.S. patent application Ser. No. 10/432,208 incorporated by reference in its entirety.

It is contemplated that the fluid waste may be separated at some point before being subjected to the waves. In embodiments that separate the waste, a portion of the waste may be diverted from contact with the waves of the RF plasma. Alternatively, portions of the waste may be subjected to the waves in succession (i.e. separately) thereby allowing for different settings to be used on different types of waste. For example, substantially solid waste can be subjected to lower frequency waves than waves that are substantially liquid. The treated waste can be discharged into a body 160 such as a lake, ocean, the ground, municipal waste treatment plant and so on. In any case, biological contamination by parasites (e.g schistosoma), protozoa (e.g *cryptosporidium parvum*), bacteria (e.g. cholera), viruses (e.g. hepatitis A), and/or metals, perchlorates and other abiotic substances is substantially reduced by exposure to the RF plasma waves. Methods of reducing 50%, 90%, or more of the microbes include the step of carrying the waste past waves produced under conditions that inactivate or kill the microbes. In generating waves using an RF plasma generator, the RF plasma generator is operated within the ranges outlined above. The waves from the RF plasma come in contact with the fluid waste thereby producing treated water. It may be desirable to further treat the treated water by subjecting the treated water to filtering, reverse osmosis, and so on. Additionally, it may be advantageous to combine additional chemicals with the treated water prior to dispensing.

Those skilled in the art will recognize that the device of FIG. 1 can be scaled up or down. For example, the device of FIG. 1 can alternatively be viewed as having multiple sources of waste and multiple waste lines, conduit, tanks, and even wave generators.

Thus, specific embodiments and applications directed toward treating a fluid waste have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A method of reducing biological contamination in an amount of waste, comprising:
    providing an RF plasma wave generator; and
    carrying the waste past waves radiated by the RF plasma wave generator under conditions in which a substantial percentage of the population of a microbe in the waste is inactivated or killed, to produce a treated waste; and
    without subjecting the waste directly to a plasma generated by the RF plasma wave generator.

2. The method of claim 1 in which the substantial percentage is at least 50%.

3. The method of claim 1 in which the substantial percentage is at least 90%.

4. The method of claim 1, further comprising treating the waste at a rate of at least 20 1/hr, and discharging the treated waste into a navigable body of water.

5. The method of claim 1, further comprising treating the waste at a rate of at least 20 1/hr, and discharging the treated waste into a sewer.

6. The method of claim 1, further comprising treating the waste at a rate of at least 20 1/hr, and discharging the treated waste into a conduit in a municipal waste treatment plant.

7. The method of claim 1, wherein the step of providing an RF plasma wave generator comprises operating the generator at a basic frequency of 0.44 MHz-40.56 MHz.

8. The method of claim 1, wherein the step of providing an RF plasma wave generator comprises operating the generator at a modulation frequency of 10-35 kHz.

9. The method of claim 1, further comprising treating the waste at a rate of at least 20 1/hr, and wherein the step of carrying the waste past the waves is carried out upon a ship.

* * * * *